United States Patent [19]

Borzatta et al.

[11] 4,340,585
[45] Jul. 20, 1982

[54] SALIFIED ANIONIC RESIN FOR CHOLESTEROL AND LIPID LOWERING

[75] Inventors: Valerio Borzatta; Manlio Cristofori, both of Bologna; Angelo Brazzi, Budrio, all of Italy

[73] Assignee: Alfa Farmaceutici, S.p.A., Bologna, Italy

[21] Appl. No.: 102,614

[22] Filed: Dec. 11, 1979

[30] Foreign Application Priority Data

Dec. 21, 1978 [IT] Italy .................... 3631 A/78

[51] Int. Cl.³ .................. A61K 31/74; C08F 8/10; C08F 8/30; C08F 8/32
[52] U.S. Cl. .................. 424/79; 424/180; 424/308; 424/317; 424/319; 521/30; 521/31; 521/32; 521/38; 536/112
[58] Field of Search .......... 424/79, 180, 308, 317, 424/319; 521/30, 31, 32, 38; 536/112

[56] References Cited

FOREIGN PATENT DOCUMENTS

| | | |
|---|---|---|
| 2151510 | 4/1972 | Fed. Rep. of Germany . |
| 2427924 | 1/1975 | Fed. Rep. of Germany . |
| 857194 | 12/1960 | United Kingdom . |
| 929391 | 6/1963 | United Kingdom . |
| 1099269 | 1/1968 | United Kingdom . |
| 1286949 | 8/1972 | United Kingdom . |
| 1460515 | 1/1977 | United Kingdom . |

OTHER PUBLICATIONS

Martindale, The Extra Pharm., Pharm. Press, London, 27th Ed., 1977, pp. 362, 366.
Cayen, Canadian J Biochem., vol. 48, 1970, pp. 1022–1023.

*Primary Examiner*—Anna P. Fagelson
*Attorney, Agent, or Firm*—Stevens, Davis, Miller & Mosher

[57] ABSTRACT

A non-toxic anionic resin selected from resins having a polymeric reticulated skeleton of styrenic or acrylic type, inert to the digestive enzymes, having a molecular weight higher than 1000 and containing ionizable amino groups, resins having a cellulosic reticulated skeleton modified by the introduction of free or substituted amino groups and resins having a polysaccharide reticulated skeleton modified by the introduction of free or substituted amino groups. The resin is capable of binding itself permanently to the biliary acids and is salified with an acid corresponding to the general formula:

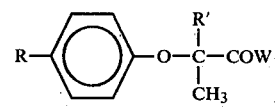

wherein:
R' represents a hydrogen atom, an alkyl group having 1 to 3 carbon atoms, a hydroxyalkyl group having 1 to 3 carbon atoms,
R represents a chlorine atom or a group selected from p-chlorobenzoyl, p-bromobenzoyl and p-fluorobenzoyl,
W represents a group selected from OH, —N(R''')—CH(R'')—(CH$_2$)$_n$—COOH and O—CH$_2$—COOH wherein n represents a number from 0 to 5, R'' represents a hydrogen atom, a benzyl, a phenyl or a phenyl substituted with an OH group, a lower alkyl, a lower alkoxyl or a lower hydroxyalkyl group and R''' represents a hydrogen atom or a lower alkyl.

5 Claims, No Drawings

SALIFIED ANIONIC RESIN FOR CHOLESTEROL AND LIPID LOWERING

The present invention relates to new products having biological activity, capable of reducing the cholesterol and triglycerides content in the blood.

The genesis of many diseases of the cardiovascular system is believed to be directly connected to high triglycerides and cholesterol contents in the blood.

Therefore many drugs capable of reducing high cholesterol and triglycerides contents in the blood to normal values have been proposed.

Among these drugs some products whose structure may be referred to that of phenoxy-methylpropionic acid are known and widely commercialized. In particular, the ethylic ester of p-chlorophenoxy-2-methylpropionic acid (Clofibrate) and the isopropylic ester of 2-[4-(p-chlorobenzoyl)phenoxy]-2-methylpropionic acid (Procetofene) are widely commercialized.

In therapeutical practice also some strong anionic resins (Colestiramine, Colestipol, etc.) are utilized, which when administered in the form of aqueous suspension, promote indirectly the reduction of the hematic cholesterol through a mechanism which comprises the fact that said resins immobilize the biliary acids present in the enteric part of the digestive tract and form insoluble irreversible complexes which are finally eliminated by the faeces.

These kinds of resins and the relevant therapeutical applications are described in British Pat. Nos. 929,391 and 1,286,949.

In German Patent Application No. 2,151,510 some mechanical mixtures of non-toxic strong anionic resins with compounds of the above-mentioned type (Clofibrate) are described. These mixtures show a hypocholesterolemic activity higher than the activities of the two components of the mixture.

It has been found, and this is the basis of the present invention, that non-toxic anionic resins, salified with acids having a structure referrable to that of phenoxymethylpropionic acid are effective in lowering and drastically reducing to normal values the excessive amounts of cholesterol and lipid present in the blood.

The therapeutical effectiveness of the products of this invention is surprisingly much higher than that of the mixtures described by the above-mentioned German patent application.

It is therefore an object of the present invention to provide new products constituted by non-toxic anionic resins salified with acids corresponding to the following general formula:

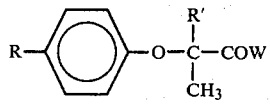

wherein:
R' represents a hydrogen atom, an alkyl group having 1 to 3 carbon atoms, a hydroxyalkyl group having 1 to 3 carbon atoms;
R represents a chlorine atom or a group selected from p-chlorobenzoyl, p-bromobenzoyl and p-fluorobenzoyl;
W represents a group selected from OH, —N(R"')—CH(R")—(CH$_2$)$_n$—COOH and O—CH$_2$—COOH wherein n represents a number from 0 to 5, R" represents a hydrogen atom, a benzyl, a phenyl or a phenyl substituted with an OH group, a lower alkyl, a lower alkoxyl or a lower hydroxyalkyl group, (the term "lower" indicates 1 to 4 carbon atoms) and R"' represents a hydrogen atom or a lower alkyl.

Some of the acids encompassed by the above general formula are new and constitute the object of Italian Patent Application No. 3630 A/78 filed on Dec. 21, 1978.

The resins which may be utilized for preparing the products according to the present invention are non-toxic synthetic polymers having a polymeric skeleton, which is of styrenic or acrylic type and is reticulated. They are inert to the digestive enzymes, have a molecular weight higher than 1000 and contain ionizable amino groups capable of binding themselves to the biliary acids. It is known that the polymeric skeleton of said resins is obtained by polymerizing styrenic or acrylic monomers in the presence of reticulating agents in amounts varying according to the desired reticulation degree (from 1 to 75% of the reticulating agent).

Ionizable amino groups are amino groups capable of forming ammonium salts substituted by reaction with acids, and quaternary ammonium salts substituted by reaction with quaternarizing agents.

Therefore the polymers to be utilized in the preparation may be in the basic form (like primary, secondary and tertiary amines), in the form of ammonium hydroxides or in the form of quaternary ammonium salts by reaction with acids. The quaternary ammonium groups have the formula $R_3N^+X^-$ wherein each R, is the same or different from the other, represents a hydrogen atom or alkyl or hydroxyalkyl groups having 1 to 5 carbon atoms. Examples of the groups are methyl, ethyl, 2-hydroxy-ethyl. $X^-$ represents a hydroxy or an anion of a physiologically acceptable acid such as chloride, sulfate, phosphate (mono-, di- or tribasic), bicarbonate, carbonate, formiate, acetate, maleate, ascorbate, fumarate, anions of amino acids such as aspartate, or polymers filled with saccharine ions.

Resins suitable for preparing the products of the present invention may be found on the market, in the anionic form, under the following trade names: Allasion, Amberlite, Chempro, De-Acidite, Diaion, Dower, Duolite, Imac, Ionac, Kastel, Lewatit, Liquonex, Mykion, Permutit, Wofatit, Zeo-Karb, Zerolit.

Other resins are of the cellulosic type, conveniently treated according to known techniques in order to introduce reactive groups, and of the polysaccharide type, preferably dextran (poly-alpha 1,6 glycane), obtained from saccharose by means of microbiological methods and subsequently reticulated by a treatment with epichlorohydrin (Sephadex, Secholex).

Suitable resins are the ones modified in such a way as to contain free or substituted amino groups.

The resins which may be utilized according to the present invention show the characteristic to bind themselves permanently to the biliary acids.

Preferred resins are the ones put on the market with the trademark "Dowex 1". They are polystyrenic resins reticulated with divinylbenzene, in the form of quaternary ammonium salts available on the market with different reticulation degrees. The "Dowex 1X2" resins (that is containing 2% of divinylbenzene as reticulating agent) in the form of chlorides are preferred.

Other preferred resins are the ones put on the market with the trademark "Sephadex DEAE and QAE" which are dextranic resins reticulated and etherified respectively with diethylaminoethyl group or 2-hydroxy-propyldiethylamino-ethyl group.

Another object of the present invention is to provide salified resins wherein the salification degree reaches the maximum value of the exchange capacity of the resin, and resins wherein the salification is limited to a fraction of their exchange capacity.

It has been found that resins salified at 2% and even at lower percentages (such as for example at 0.7%) provide satisfactory results.

The salified resins of the present invention may be utilized as drugs, orally administrable, in order to lower the cholesterol and lipid content in the blood. The minimum effective dose daily administrable to the man is about 10 g. However, owing to the low degree of toxicity of the salified resins of this invention, it is possible to adminster even higher daily doses. The preferred dose is comprised between 12 and 30 g. The salified resins according to this invention may be administered in the form of conventional pharmaceutical preparations such as syrups, suspensions, etc., containing additives like: excipients, preserving agents, lubricants, stabilizers, dampening agents, emulsifying agents, salts suitable to modify the osmotic pressure, buffers, dyes, flavors and sweeteners.

(a) METHOD FOR ACTIVATING THE RESIN

The anionic resin is washed, in order with aqueous hydrochloric acid 0.1 N, distilled water and sodium hydroxide 0.1 N solution. The washing is carried out by suspending the resin in the washing liquid, decanting the resin and eliminating the overflow. The sequence of washings is repeated three times. The resin is washed again with hydrochloric acid 0.1 N and then with distilled water until reaching a neutral reaction. The washed resin is kept in a humid state up to the time of its use.

The activation method may be carried out with acids other than hydrochloric acid.

(b) METHOD FOR SALIFYING THE RESIN

A chromatographic column of 1 cm diameter, is filled for the height of 2 cm with the anionic resin washed as above described under (a).

The maximum exchange capacity may be calculated from the volume of the resin and from the specific exchange capacity of the resin.

The acid to be salified with the resin is solved into an equivalent amount of sodium hydroxide solution of 1 N and the solution is poured into the column. The system is eluted with distilled water up to the absence of anions.

The so salified resin may be utilized either in the humid form, as obtained from the salifying reaction, it may be diluted thus obtaining a suspension, or it may be dried and kept in the dry form.

(c) DETERMINATION OF SALIFICATION DEGREE OF BASIC GROUPS OF THE RESIN

An aqueous suspension of an anionic resin, activated as described under (a), is fed into a chromatographic column and treated with a solution of the acid to be salified with the resin, the acid being dissolved in an equivalent amount of sodium hydroxide.

Then the system is eluted with water and all the elution is collected. The anion present in the elution is titrated and the salification percentage may be calculated from the ratio between the so determined value and the content of anions initially present in the resin.

(d) DETERMINATION OF THE DECREASE OF TRIGLYCERIDES CONTENT IN THE SERUM OF RATS BASED ON HYPERTRIGLYCERIDAEMIA CAUSED BY FRUCTOSE

Male Wistar rats weighing 250±20 g, normally fed, and subdivided in groups of 6 animals each, are used. The products to be evaluated, either dissolved in propylene glycol or suspended in water, are administered orally, by means of a gastric probe, at a dosage corresponding to 0.05 millimoles of acid/Kg in 5 ml/Kg of solvent or suspendant.

The animals are treated with the product to be evaluated for 3 days. In the first day they are kept without drinking water, while in the two following days they receive drinking water in the form of a 20% solution of fructose.

The animals are sacrificed under ethereal anaesthesia and the blood is drawn by an intercardiacal injection. The triglycerides are determined in the serum according to Eggstein, F. H. Kreutz and F. H. Schmidt (Eggstein, M and F. H. Kreutz, Klin. Wschr., 44, 262 (1966); Schmidt, F. H. and K. Von Dahl. Z. Klin. Chem. 6, 156 (1968)).

(e) DETERMINATION OF THE VARIATION OF HEMATIC CHOLESTEROL CONTENT AND OF HEPATIC CHOLESTEROL CONTENT IN THE RAT

Male Wistar rats weighing 280±20 g, normally fed, and subdivided in groups of 6 animals each, are used. The products to be evaluated, either dissolved in propylene glycol or suspended in water, are administered orally, by means of a gastric probe, at a dosage corresponding to 0.6 millimoles/Kg of acid dissolved or suspended in a volume of 5 ml/Kg.

The animals are sacrificed at the fixed times and the blood is drawn by an intercardiacal injection. The cholesterol content is determined in the serum. At the same time the hepatic cholesterol is also determined. The cholesterol dosage is carried out according to D. Watson, Clin. Chim. Acta 5, 637 (1960).

(f.) DETERMINATION OF THE VARIATION OF TOTAL LIPIDES, OF TOTAL CHOLESTEROL AND OF TRIGLYCERIDES IN RATS FED WITH GREENNBERG HYPERCHOLESTEROLEMIC DIET MODIFIED ACCORDING TO TENSHO ET AL.

Male Wistar rates, weighing 90 to 100 g, are fed for 7 days with Tensho et al hypercholesterolemic diet (Acutely induced hypercholesterolemia in the rat—Yakugaku Zasshi 1972—92, 879).

During the last 3 days the rats are orally treated, twice a day, with 650 mg/Kg of the products according to the present invention. After 17 hours of fast, the haematic levels of totals cholesterol, total triglycerides and lipides are determined according to the methods described respectively by Watson, D. Clin. Acta 5, 637, (1960); Eggstein, M. Klin. Wschr. 44, 267 (1966); Zoellner, N. and K. Kirsch Z. gss. exp. Med. 135, 545 (1962).

The following examples are supplied for the purpose of illustrating the invention.

EXAMPLE 1

According to the procedure previously described under (a) and (b), 6 g of Dowex 1-X-2 resin, of a size passing through 100–200 mesh standard screen size (marketed by Dow Chemical Co.), having a specific exchange capacity of 3.5 meq/g, are washed and salified with 2-[4-(p-chlorobenzoyl)phenoxy]-2-methylpropionic acid (free acid of Procetofene, hereinafter indicated as "procetofenic acid") (1 g: 3.14 meq) solved in a 1 N sodium hydroxide solution (3.14 ml). The acid amount is enough to saturate the 15% of exchange capacity of the resin.

EXAMPLE 2

Following the same method and starting from appropriate amounts of the same reactants, a product saturated at 2.38% of the exchange capacity was obtained. The capability of this product in lowering the triglycerides in rats affected by hypertriglyceridemia induced by fructose is determined. The technique is described under (d).

Table I shows the variations in percent of triglycerides content in the blood referred to the rats treated with only fructose.

TABLE I

| Product | Daily dose | Variation % |
|---|---|---|
| Example 2 | 616 mg/Kg | −79 |
| Dowex 1X2 resin | 600 mg/Kg | −18 |
| Sodium salt of procetofenic acid | 15.9 mg/Kg (=0.05 m.moles/Kg) | −63 |
| Mechanical mixture Dowex 1X2 resin (600 mg) and sodium salt of procetofenic acid (15.9 mg) | 616 mg/Kg | −57 |

The capability of influencing the hematic and hepatic cholesterol content in the rat according to the technique described under (e) has been determined.

Table II shows the variations in percent of cholesterol content at different times in comparison with the untreated rats.

TABLE II

| | | Variation % of cholesterol content | | | | | |
|---|---|---|---|---|---|---|---|
| | | Hepatic | | | Hematic | | |
| Product | Daily dose | 7 h | 24 h | 48 h | 7 h | 24 h | 48 h |
| Product of Example 1 | 800 mg/Kg | −16 | −15 | −11 | +8 | −43 | −36 |
| Dowex 1X2 resin | 600 mg/Kg | +6 | −3 | −7 | +9 | +7 | +29 |
| Sodium salt of procetofenic acid | 200 mg/Kg =0.6 m.moli/Kg | −17 | +25 | −7 | 0 | −37 | −26 |
| Mechanical mixture Dowex 1X2 resin (600 mg) and sodium salt of procetofenic acid (200 mg) | 800 mg/Kg | −4 | +7 | −23 | −11 | −33 | −15 |

As it may be seen, the product according to this invention differs decidedly from the mechanical mixture resin/procetofenic acid and is decidedly more active both in lowering triglycerides in the fructose test and in lowering the cholesterol content in the blood.

In particular the decrease of the hematic cholesterol is not joined with any increase of the hepatic cholesterol. By examining Table II it is noted that the hepatic cholesterol decreases after seven hours and remains at that level without further substantial modifications.

EXAMPLE 3

Following the same working conditions previously described under (a) and (b), 6 g of Dowex 1X2 resin (100–200 mesh), having a specific exchange capacity of 3.5 meq/g, were reacted with 0.5 g of procetofenic acid, up to a saturation of 7.48% of the exchange capacity of the resin. The activity of the product was determined with the above described method (f) and was compared with the activity of the same quantity of resin, with the same quantity of sodium salt and of procetofenic acid (Table III).

TABLE III

| | | Decrease % with respect untreated rats | | |
|---|---|---|---|---|
| Product | Daily dose | Total Lipides | Total Cholesterol | Total Triglycerides |
| Dowex 1X2 resin saturated at 7.48% | 2 × 650 mg/Kg | −43 | −42 | −56 |
| Dowex resin 1X2 | 2 × 600 mg/Kg | −21 | −30 | −27 |
| Sodium salt of procetofenic acid | 2 × 50 mg/Kg | −39 | −36 | −46 |
| Mechanical mixture Dowex 1X2 resin and sodium salt of procetofenic acid | 2 × 650 mg/Kg | −37 | −35 | −41 |

EXAMPLE 4

6 g of Sephadex DEAE A-25 resin, as particles of diameter 40–120 microns, having a specific exchange capacity of 3.5±0.5 meq/g at the dry state, were salified with 1 g of 2-[4-(p-chlorobenzoyl)phenoxy]-2-methyl-propionic acid solved in 1 N sodium hydroxide, as described in Example 1, thus obtaining a resin salified at 15% of exchange capacity, whose capability in lowering the cholesterol and triglycerides contents in the blood is comparable with that of the product of Example 2.

EXAMPLE 5

According to the method previously described under (a) and (b), a Dowex 1-X-2 resin with a specific exchange capacity of 3.5 meq/g, finely ground (smaller than 200 mesh standard screen size) was used. The resin was salified with procetofenic acid to obtain a product saturated at 1.99% of the exchange capacity. The capability of lowering total cholesterol and total lipides, both hepatic and hematic, in rats affected by hypercholesterolaemia caused by Greenbey diet modified according to Tensho was determined. The technique is described under (f). The results are shown in the following Table IV.

TABLE IV

| Product | Daily dose | Variation % of cholesterol content with respect to the value of the diet | | Variation % of lipides content with respect to the value of the diet | |
| --- | --- | --- | --- | --- | --- |
| | | hepatic | hematic | hepatic | hematic |
| Example 5 | 2.30 g/Kg | −57 | −50 | −57 | −73 |
| Dowex 1-X-2 resin | 2.25 g/Kg | −43 | −70 | −27 | −89 |
| Sodium salt of procetofenic acid | 50 mg/Kg as acid | −31 | −51 | −36 | −73 |
| Procetofene | 50 mg/Kg | −29 | −58 | −40 | −86 |
| Clofibrate | 50 mg/Kg | +13 | −24 | +14 | −48 |

What is claimed is:

1. A non-toxic cholestyramine resin, said resin being capable of binding itself permanently to the biliary acids, said resin being salified with an acid corresponding to the general formula:

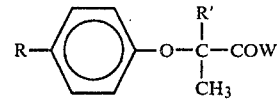

wherein:
R' represents a hydrogen atom, an alkyl group having 1 to 3 carbon atoms, a hydroxyalkyl group having 1 to 3 carbon atoms,
R represents a chlorine atom or a group selected from the group consisting of p-chlorobenzoyl, p-bromobenzoyl and p-fluorobenzoyl,
W represents a group selected from the group consisting of OH, —N(R''')—CH(R'')—(CH$_2$)$_n$—COOH and O—CH$_2$—COOH wherein n represents a number from 0 to 5, R'' represents a hydrogen atom, a benzyl, a phenyl or a phenyl substituted with an OH group, a lower alkyl, a lower alkoxyl or a lower hydroxyalkyl group and R''' represents a hydrogen atom or a lower alkyl.

2. The resin according to claim 1 wherein the salification degree is 0.7% to 100% of the exchange capacity of the resin.

3. The resin according to claim 2 wherein the salifying acid is 2-[4-(p-chlorobenzoylphenoxy]-2-methylpropionic acid.

4. The resin according to claim 3 is in the form of a polystyrenic resin reticulated with 2% of a divinyl benzene chloride.

5. A pharmaceutical preparation orally administrable to lower the cholesterol and lipid content in the blood, containing as an active substance the salified resin of any one of claims 1–4 in an effective dosage amount therefor, together with adjuvants.

* * * * *

UNITED STATES PATENT AND TRADEMARK OFFICE
CERTIFICATE OF CORRECTION

PATENT NO. : 4,340,585
DATED : July 20, 1982
INVENTOR(S) : Borzatta et al.

It is certified that error appears in the above-identified patent and that said Letters Patent is hereby corrected as shown below:

Column 2, line 46 change "Dower" to -- Dowex--.

Column 3, line 25 change "lubrificants" to --lubricants--.

Column 3, line 52 change "solution of 1 N" to --solution 1 N--.

Column 4, line 55 change "rates" to --rats--.

Signed and Sealed this

Thirtieth Day of October 1984

[SEAL]

Attest:

Attesting Officer

GERALD J. MOSSINGHOFF

Commissioner of Patents and Trademarks